(12) United States Patent
Gu et al.

(10) Patent No.: US 9,033,882 B2
(45) Date of Patent: May 19, 2015

(54) GAS SUPERSATURATION MONITORING

(75) Inventors: Alex Gu, Plymouth, MN (US); Wei Yang, Minnetonka, MN (US); Peter Tobias, Minnetonka, MN (US)

(73) Assignee: Honeywell International Inc., Morristown, NJ (US)

( * ) Notice: Subject to any disclaimer, the term of this patent is extended or adjusted under 35 U.S.C. 154(b) by 481 days.

(21) Appl. No.: 12/797,982

(22) Filed: Jun. 10, 2010

(65) Prior Publication Data

US 2010/0317970 A1    Dec. 16, 2010

Related U.S. Application Data

(60) Provisional application No. 61/185,921, filed on Jun. 10, 2009.

(51) Int. Cl.
| | |
|---|---|
| *A61B 8/00* | (2006.01) |
| *A61B 5/1455* | (2006.01) |
| *B63C 11/18* | (2006.01) |
| *A61B 8/08* | (2006.01) |

(52) U.S. Cl.
CPC ............ *A61B 5/14551* (2013.01); *B63C 11/18* (2013.01); *A61B 8/4472* (2013.01); *A61B 8/481* (2013.01)

(58) Field of Classification Search
CPC .. A61B 5/14551; A61B 5/726; A61B 5/7214; A61B 8/481; A61B 8/4472; A61B 8/06; G01L 11/04; G01S 15/8979; G01S 7/52038; G01S 2291/02872; G06F 17/40; G06K 9/0051; H04B 1/123; A61K 49/223

USPC .......................................................... 600/438
See application file for complete search history.

(56) References Cited

U.S. PATENT DOCUMENTS

| | | | |
|---|---|---|---|
| 4,290,432 A | 9/1981 | Daniels | |
| 4,483,345 A * | 11/1984 | Miwa | ............................ 600/438 |
| 4,657,756 A * | 4/1987 | Rasor et al. | .................. 424/9.52 |
| 4,882,678 A | 11/1989 | Hollis et al. | |
| 5,457,284 A | 10/1995 | Ferguson | |
| 5,503,145 A * | 4/1996 | Clough | ..................... 128/204.22 |
| 5,579,284 A * | 11/1996 | May | .............................. 367/132 |
| 6,321,177 B1 | 11/2001 | Ferrero et al. | |
| 6,322,512 B1* | 11/2001 | De Jong et al. | ............... 600/458 |
| 6,629,449 B1 | 10/2003 | Kline-Schoder et al. | |
| 6,931,348 B2 | 8/2005 | Furuta et al. | |
| 2004/0040379 A1* | 3/2004 | O'Donnell et al. | ............. 73/627 |
| 2004/0236196 A1* | 11/2004 | Diab et al. | ..................... 600/310 |
| 2006/0020208 A1 | 1/2006 | Egozi | |

OTHER PUBLICATIONS

Crum et al., Monitoring bubble growth in supersaturated blood and tissue ex vivo and the relevance to marine mammal bioeffects, Acoustical Society of America, 2005, 6 (3), p. 214-220.*

(Continued)

*Primary Examiner* — Long V Le
*Assistant Examiner* — Bo J Peng
(74) *Attorney, Agent, or Firm* — Schwegman Lundberg & Woessner, P.A.

(57) ABSTRACT

A system and method include generating at least one bubble in tissue using ultrasound. The at least one bubble generated is detected and correlated to gas saturation of the tissue.

6 Claims, 4 Drawing Sheets

(56) References Cited

OTHER PUBLICATIONS

"Fathom Systems: Gas Analysing Equipment in Commercial Saturation Diving Systems", http://www.fathomsystems.co.uk/files/images/SP-REP-0022-121-100-00__A.pdf, Technical Report, (Sep. 24, 2006), 21 pgs.

"U.S. Navy Diving Manuel—Revision 6", http://www.supsalv.org/pdf/DiveMan_rev6.pdf, Published by Direction of Commander, Naval Sea Systems Command, (Apr. 15, 2008), 992 pgs.

* cited by examiner

GAS SUPERSATURATION MONITORING

RELATED APPLICATION

This application claims priority to U.S. Provisional Application Ser. No. 61/185,921 (entitled GAS SUPERSATURATION MONITORING FOR DIVERS, filed Jun. 10, 2010) which is incorporated herein by reference.

BACKGROUND

Divers need real-time blood gas level monitoring to maintain their wellbeing, especially during the ascending operation. For example, ascending too fast may result in symptoms such as decompression sickness, commonly referred to as the bends. Real-time monitoring of the gas saturation level of the diver's blood enables the diver to control the ascending speed according to its physiological condition, greatly reduces the risks of bends and increase the flexibility of the diver. Unfortunately, current divers rely on empirical diving tables, a one size fits all solution. Aircraft personnel can experience similar problems when ascending to high altitude if their cabin is not pressurized enough.

DETAILED DESCRIPTION

Figure 1:
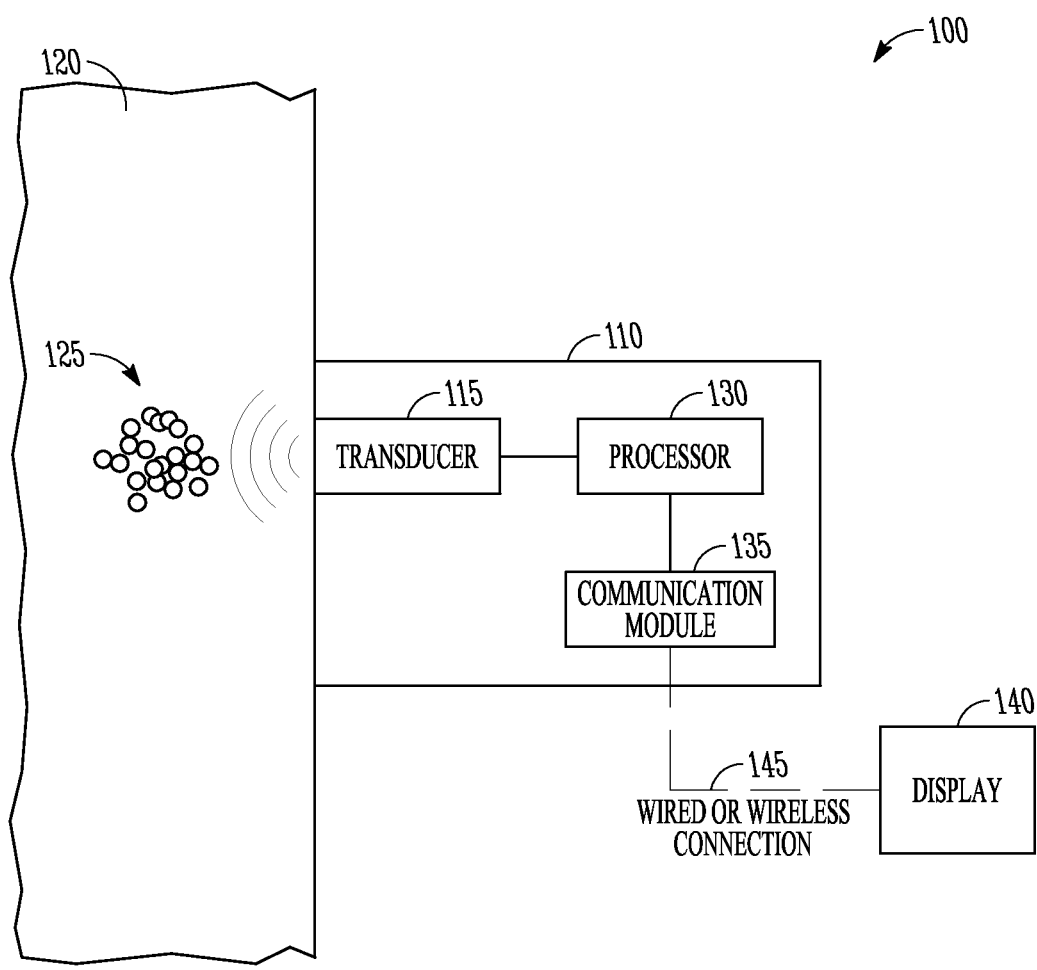
FIG. 1 is a block diagram of a gas saturation measuring system according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical, and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and hardware in one embodiment. Functions correspond to modules, which are software, hardware, firmware, or any combination thereof. Multiple functions may be performed in one or more modules as desired, and the embodiments described are merely examples. The software may be executed on a digital signal processor, ASIC, microprocessor, or other type of processor operating on a computer system, such as a microcontroller, personal computer, server or other computer system.

A system and method monitors real time blood gas saturation levels of divers at different immersion depths. In the following, only divers are referred to, as they experience large pressure drops, but the system and method is also applicable for aircraft personnel or in other situations where pressure drops may be experienced. In various embodiments, blood-dissolved gas is transformed into bubbles through cavitations induced by a miniaturized ultrasound source. The induced gas bubbles are then detected by a detector embedded in a divers gear or equipment, such as the mouth piece. In one embodiment, the bubble detector utilizes the same ultrasound source used for bubble generation in a pulse-echo mode at a much lower power level. Changes in acoustic reflectivity and/or impedance are measured, and correlated to the presence of an induced bubble or bubbles. In other embodiments, two or multiple different ultrasound frequencies and power levels may be used. One or more frequency or power level may be used for generating the bubbles, and another one or more frequency and power levels may be used for detecting bubbles. In some embodiments, the sound of collapsing microbubbles may be sensed, and contains information of the bubble formation kinetics. At high saturation of nitrogen, fewer bubbles collapse.

The system may be coupled to a dive computer, such as a wrist worn device via wired or wireless connection. In some embodiments, the dive computer may receive measurements and perform calculations to determine gas saturation. A display may be used to provide information to the diver regarding rate of ascent, such as "proceed", "slow down", "stop", etc. The information could also be sent wirelessly to accompanying divers, like the dive leader, or to a base station, like a ship via a wireless network. The system will give warning well before massive bubble are generated due to ultrasound induced bubble growth.

Ultrasound is routinely used in diagnostics, e.g. for fetuses, and should not be dangerous for the diver. The tiny bubbles that are generated in tissue, such as lips or tongues quickly dissolve. Even if they do not dissolve quickly, they enter veins and flow back to the heart, not the brain, and are not a danger in themselves. The sensor may be incorporated into the mouth piece, ear piece, or other part of the diver for real-time monitoring of the blood gas super saturation level.

In some embodiments, active generation of 1-3 μm diameter supersaturated gas bubbles may be performed at frequencies of approximately 1-3 MHz ultrasound in a 1 $mm^2$ area of the inner side of the lips/cheek, or other tissue. A pulse-echo mode of ultrasound may be used to monitor the dissolution kinetics of the generated gas bubbles. An approximately ~10 us ultrasound pulse in one embodiment has minimal heat effect of the interrogated blood vessel and tissue. Other length pulses may also be used in further embodiments. A ~3 μm diameter generated bubble will re-dissolve in ~40 ms when the ultrasound is off, leaving no adverse health effect. A change of the ultrasound echo scattering intensity and its decay kinetics may be used to determine the degree of gas oversaturation of the body. Actual measurements for each system with various frequency and duration parameters for the ultrasound may be used to establish thresholds for over saturation.

In FIG. 1, a system 100 includes a gas sensor 110 that includes a transducer 115. The gas sensor 110 is adapted to be worn by a diver adjacent to tissue 120 of the diver. The transducer in one embodiment includes an ultrasound generator adapted to be placed proximate living tissue 120 for inducing bubble formation 125 in tissue. The transducer 115 may also be used as a bubble detector that is adapted to be placed proximate the tissue 120 to detect the bubbles 125 induced in the tissue.

In one embodiment, the ultrasound generator emits bubble generating megahertz range pulses at a first high power level to induce bubble formation in the tissue. The power level is sufficient to cause the formation of one to thousands of bubbles without damaging the tissue. The bubble detector emits interrogation megahertz sound pulses at a much lower power, and detects echoes from bubbles in the tissue.

Transducer 115 may be coupled to circuitry 130, such as a programmed microprocessor 130 or other circuitry for controlling generation of the pulses by the transducer 115. In one embodiment, circuitry 130 receives information corresponding to the sensed bubbles and processes the information to determine the amount of gas saturation of the blood or tissue. In one embodiment, the processed information is correlated to the amount of gas saturation and whether a diver can ascend more quickly, less quickly, or whether the diver should stop. In one embodiment, circuitry 130 has stored information or is receiving it from another system about the composition of the used breathing gas, e.g. the ratio of helium to nitrogen, and uses the information to fine-tune its recommendation whether a diver can ascend more quickly, less quickly, or whether the diver should stop. Certain compositions of gas are known to reduce the risk of adverse bubble formation, and ascension rates may be increased when such compositions are in use.

The correlated information may be converted to instructions for the diver and provided to the diver via a communication module 135 to a display 140. The communication module may be a wired or wireless transducer in communication with the display as indicated at 145. The display may be a diver watch, a gage, a display in a diver mask, or other type of display visible to the diver to assist with the rate of ascent. The display provides information to the diver that may include the amount of gas saturation and whether a diver can ascend more quickly, less quickly, or whether the diver should stop. A display may also be located at an accompanying diver, like the dive leader, or at a base station, like a ship.

Figure 2:
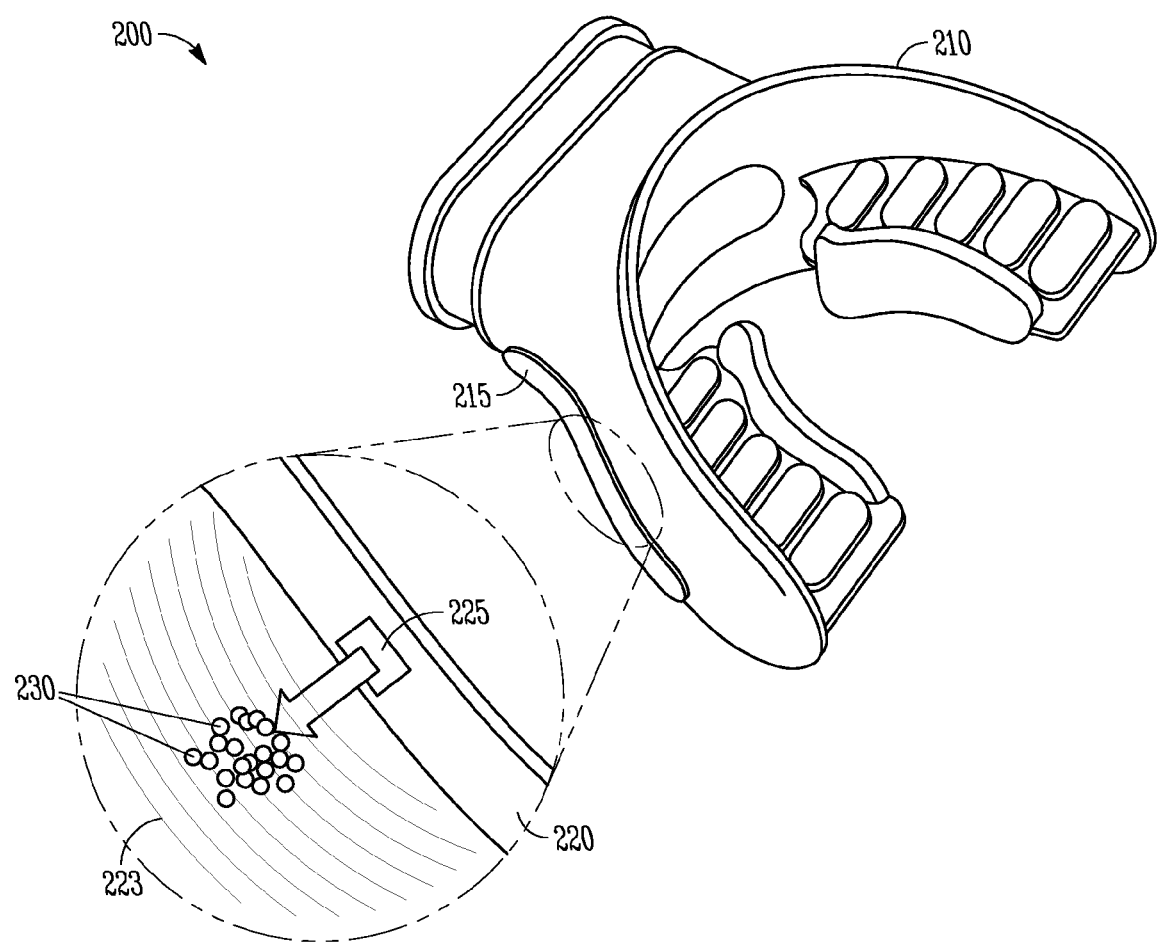
FIG. 2 is a diagram of a gas saturation measuring system incorporated in a diving mouthpiece according to an example embodiment.

FIG. 2 is a diagram of a gas saturation measuring system 200 incorporated in a diving mouthpiece 210 according to an example embodiment. A portion 215 of the mouthpiece 210 is shown in blown up form at 220. The portion 215, 220 is located on an outside portion of the mouthpiece 210 that is normally in contact with cheek tissue 223 such as the inner side of the lips of a diver. An ultrasound transceiver 225 is embedded in the portion 215, 220 and emits bubble generation sound waves and bubble detection sound waves, and also senses reflected bubble detection sound waves. Generated bubbles are illustrated generally at 230 and are exaggerated in size for illustration purposes.

Transducer 225 may include circuitry for controlling generation of the pulses and processing sensed information to correlate the sensed information to the amount of gas saturation and whether a diver can ascend more quickly, less quickly, or whether the diver should stop.

The correlated information may be converted to instructions for the diver and provided to the diver via a communication module 135 to a display 140. The communication module may be a wired or wireless transducer in communication with the display. The display may be a diver watch, a gage, a display in a diver mask, or other type of display visible to the diver to assist with the rate of ascent. The display provides information to the diver that may include the amount of gas saturation and whether a diver can ascend more quickly, less quickly, or whether the diver should stop. A display may also be located at an accompanying diver, like the dive leader, or at a base station, like a ship.

Figure 3:
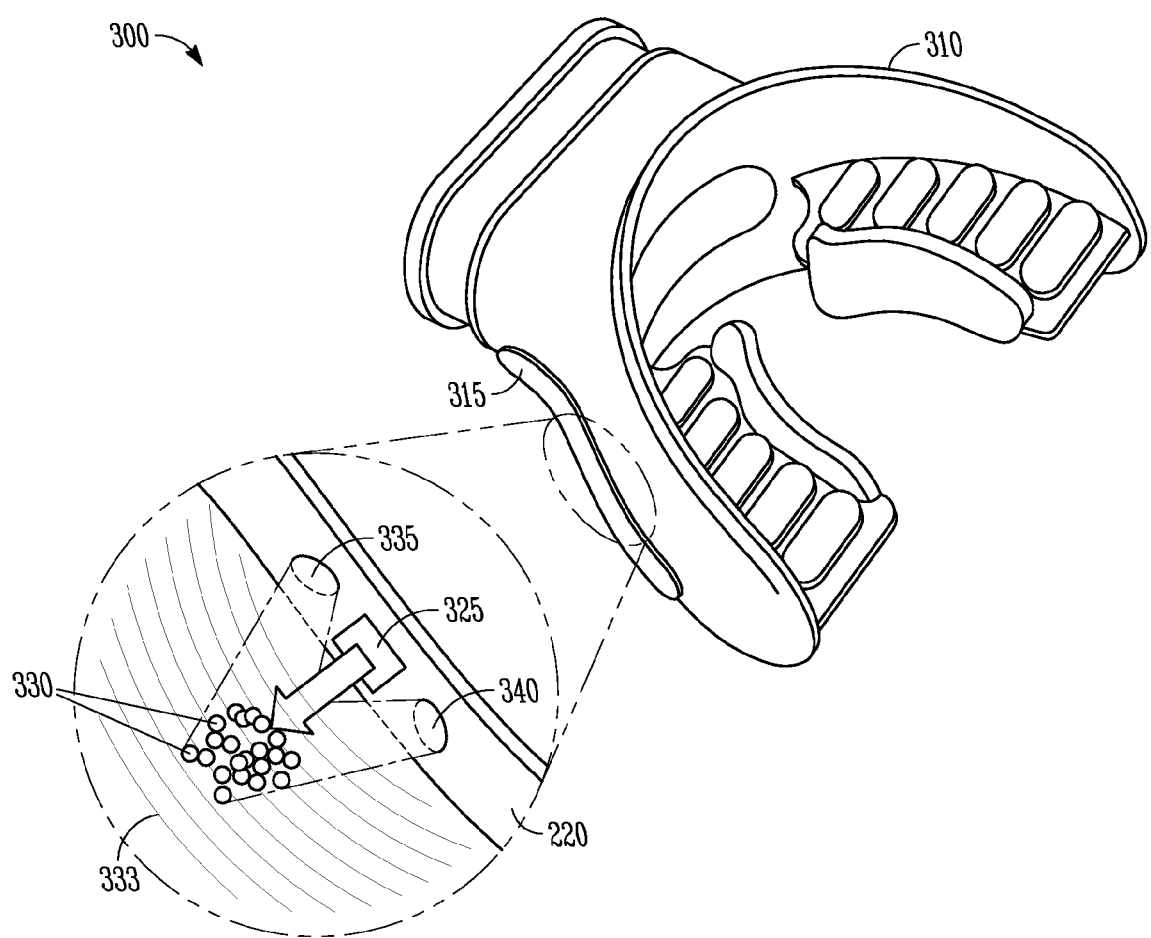
FIG. 3 is a diagram of an alternative gas saturation measuring system incorporated in a diving mouthpiece according to an example embodiment.

FIG. 3 is a diagram of an alternative gas saturation measuring system 300 incorporated in a diving mouthpiece 310 according to an example embodiment. A portion 315 of the mouthpiece 310 is shown in blown up form at 320. The portion 315, 320 is located on an outside portion of the mouthpiece 310 that is normally in contact with cheek tissue 323 such as the inner side of the lips of a diver. An ultrasound transceiver 325 is embedded in the portion 315, 320 and emits bubble generation sound waves. Generated bubbles are illustrated generally at 230 and are exaggerated in size for illustration purposes. In one embodiment, an optical source 335 is provided to illuminate the bubbles, like an infrared (IR) source. A photodetector 340 is used to sense light scattering from the illuminated bubbles 330.

Transducer 325 may include circuitry for controlling generation of the pulses and processing sensed information to correlate the sensed information to the amount of gas saturation and whether a diver can ascend more quickly, less quickly, or whether the diver should stop. The correlated information may be converted to instructions for the diver. A display may also be located at an accompanying diver, like the dive leader, or at a base station, like a ship.

Figure 4:
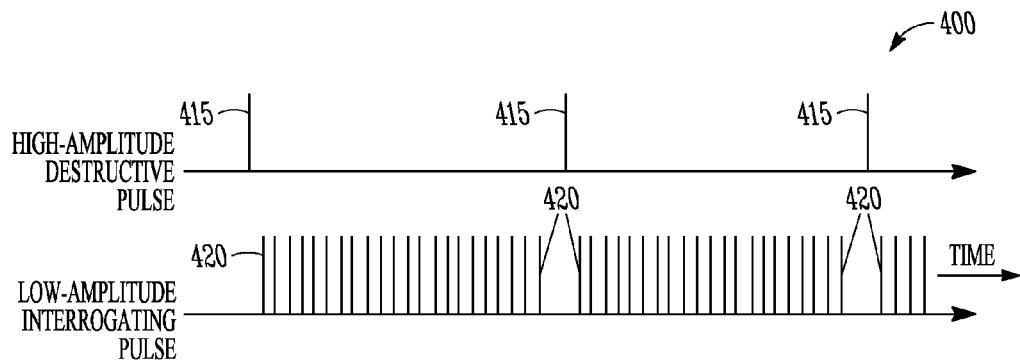
FIG. 4 is a pair of graphs illustrating timing of bubble generation pulses and interrogating pulses according to an example embodiment.

A method of sensing gas saturation levels is illustrated graphically in FIG. 4 at 400. A series of bubble generation pulses 410 in one embodiment consists of approximately ~10 µs ultrasound pulses 415 focused on 1-3 $mm^2$ of tissue having minimal heat effect of the interrogated blood vessel or tissue. Other length pulses may also be used in further embodiments. One to thousands of bubbles may be generated by the bubble generation pulses.

A ~3 µm diameter generated bubble will re-dissolve in ~40 ms when the ultrasound is off in unsaturated blood or tissue. This time may vary with the size of the bubbles. With a given power and frequency, the bubble size remains constant, and the rate of dissolving is directly representative of the gas saturation of the tissue. Bubbles appear to be highly resonant. A given driving ultrasound frequency determines the dominant bubble size; e.g. 1 MHz ultrasound generates ~3 um diameter bubbles with certain size distribution. Dissolution of the generated bubble is dependent on the degree of supersaturation of gas in the tissue.

Interrogation pulses are illustrated at 420 and begin shortly after each bubble generation pulses 410. In some embodiments, the interrogation pulses may be provided by a separate ultrasound generator, and may be continuous in nature, either at the same frequency or a different frequency. As the generated bubbles dissolve back into the tissue and blood, the return received from the interrogation pulses also decreases representative of the rate of the bubbles dissolving—the length of the life of the bubbles. Since the rate of the bubbles dissolving is a function of the amount of gas saturation of the blood, the return from the interrogation pulses is representative of the amount of gas saturation.

Various power levels may be used in different embodiments. Generally, the interrogation pulses 420 are at a power level lower or much lower than the bubble generation pulses. In one embodiment, the interrogation pulses are approximately one thousandth the power level of the bubble generation pulses 415 to ensure that the interrogation pulses do not themselves generate further bubbles. The proper power levels may be determined empirically in some embodiments, and may be dependent on the size of bubbles desired and frequency used to generate the bubbles. Generally, the frequency may be in the 1-5 MHz range. In further embodiments, the frequency by be from 100 KHz to 1 GHz.

In further embodiments, detection may be done by a separate source using a separate ultrasound source, or other detection mechanism responsive to the induced bubbles, such as an optical scattering based device. In one embodiment, a flow cytometer may be used that detects changes in signal scattering caused by the bubbles.

Figure 5:
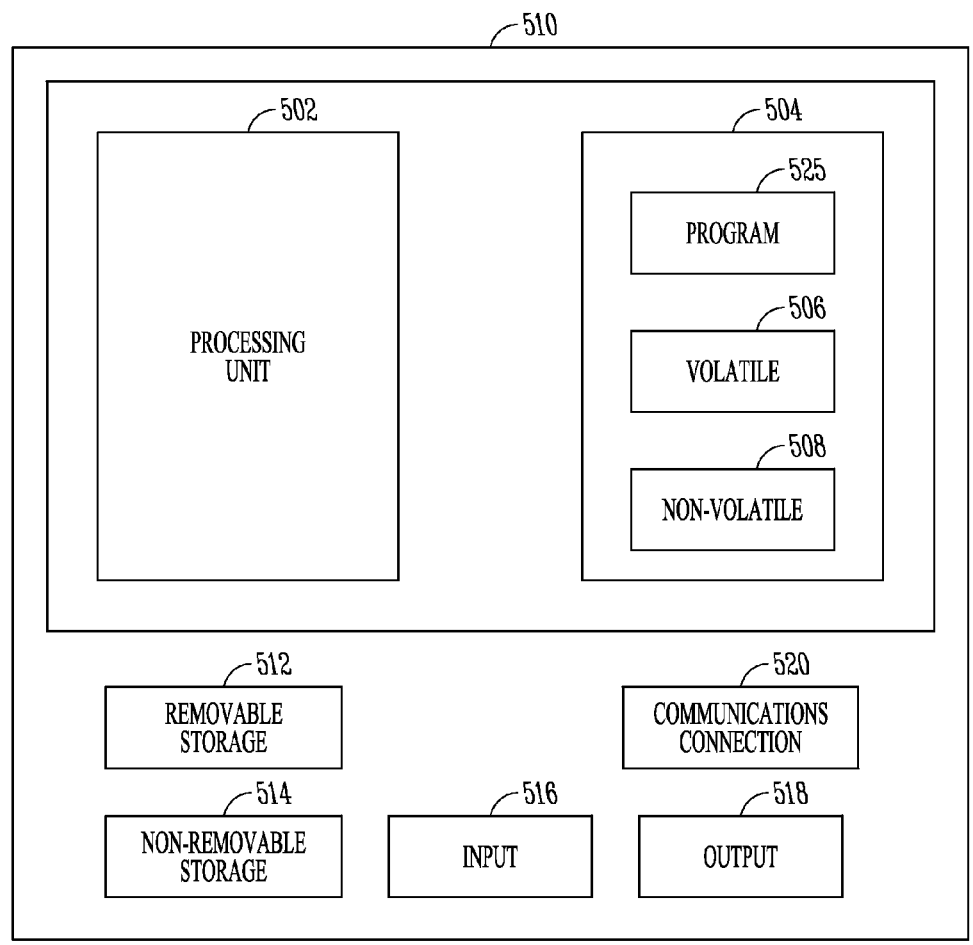
FIG. 5 is a block diagram of a computer system that executes programming according to example embodiments.

A block diagram of a computer system that executes programming for performing the above algorithm is shown in FIG. 5. A general computing device in the form of a computer 510, may include a processing unit 502, memory 504, removable storage 512, and non-removable storage 514. Memory 504 may include volatile memory 506 and non-volatile memory 508. Computer 510 may include—or have access to a computing environment that includes—a variety of computer-readable media, such as volatile memory 506 and non-volatile memory 508, removable storage 512 and non-removable storage 514. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Computer 510 may include or have access to a computing environment that includes input 516, output 518, and a communication connection 520. The computer may operate in a networked environment using a communication connection to connect to one or more remote computers. The remote computer may include a personal computer (PC), server, router, network PC, a peer device or other common network node, or the like. The communication connection may include a Local Area Network (LAN), a Wide Area Network (WAN) or other networks. Output 518 in one embodiment comprises a display, such as a display that provides a diver with information about length of dive, depth, and other information. In one embodiment, the computer 510 is coupled to the ultrasound transducer, and is programmed to provide information responsive to detected gas saturation to allow the diver to properly decompress on ascent.

Conclusion:

A miniaturized ultrasound source is used to generate ~3 µm diameter gas bubbles in blood and/or tissue. Generated bubble size and dissolution kinetics are monitored using the same ultrasound source, where the bubble size and dissolution kinetics are correlated to the gas supersaturation level in blood. In some embodiments, active generation of ~µm diameter sized supersaturated gas bubbles through ~1 MHz ultrasound is performed in a 1 $mm^2$ area of the inner side of the lips/cheek. Pulse-echo ultrasound may be used to monitor the dissolution kinetics of the generated gas bubble. A ~3 µm diameter generated bubble re-dissolves in ~40 ms when the ultrasound is off. The change of the ultrasound echo scattering intensity and its decay kinetics are used to determine the degree of gas supersaturation of the body.

Benefits that may be provided by some embodiments include real-time (~1 sec) information of the degree of supersaturation of the dissolved gases for the diver; prevent decompression sickness (e.g. the bends). Some embodiments provide a universal monitoring platform for divers on any mixture of gases. Real-time suggestions may be provided to the diver with possible course of action during ascending. Individual variations of divers towards the empirical diving tables may be eliminated in some embodiments.

The Abstract is provided to comply with 37 C.F.R. §1.72(b) is submitted with the understanding that it will not be used to interpret or limit the scope or meaning of the claims.

The invention claimed is:

1. A system comprising:
a scuba mouthpiece including:
an ultrasound generator adapted to be placed proximate living tissue to induce bubble formation in the tissue; and
a bubble detector adapted to be placed proximate the tissue to detect bubbles induced in the tissue; and
processing circuitry coupled to the bubble detector to calculate the rate of the bubbles dissolving and gas saturation in the living tissue in real-time, of a diver at an immersion depth.

2. The system of claim 1 wherein the bubble detector emits light and measures light scattering due to bubbles in the tissue.

3. The system of claim 1 wherein the ultrasound generator and bubble detector are integrated into the scuba mouthpiece such that the ultrasound generator and the bubble detector are adjacent to a tongue, lip or cheek tissue of the diver.

4. The system of claim 1 and further comprising a display coupled to the processing circuitry to provide information to at least one of a diver, accompanying divers, and a base station, as a function of the detected bubbles.

5. The system of claim 1 wherein the processing circuitry uses information about the composition of the breathing gas, stored in its memory or received from another system, to improve its calculations of gas saturation of tissues.

6. A system comprising:
a scuba mouthpiece including a transducer adapted to generate a first plurality of pulses to generate bubbles in living tissue and to generate a second plurality of pulses to detect bubbles in living tissue
processing circuitry coupled to the transducer to control generation and detection of the bubbles and to calculate the rate of the bubbles dissolving and the gas saturation in the living tissue in real time; and
a display coupled to the circuitry to provide information in real time regarding ascent to a diver wearing the transducer;
wherein the power of the first plurality of pulses for generating bubbles is greater than the power of the second plurality of pulses for detecting the generated bubbles.

* * * * *